United States Patent
Bazin et al.

(12) 
(10) Patent No.: US 6,251,412 B1
(45) Date of Patent: Jun. 26, 2001

(54) COSMETIC COMPOSITION COMPRISING PIGMENTS AND AN ANTIPERSPIRANT AND USE OF SUCH A COMPOSITION

(75) Inventors: Roland Bazin, Bievres; Isabelle Bara, Paris, both of (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/356,336

(22) Filed: Jul. 19, 1999

(30) Foreign Application Priority Data

Jul. 17, 1998 (FR) .................................................. 98 09155

(51) Int. Cl.⁷ ................................. A61K 7/00; A61K 7/32
(52) U.S. Cl. ............................ 424/401; 424/65; 424/400
(58) Field of Search ............................... 424/401, 65, 400

(56) References Cited

U.S. PATENT DOCUMENTS

| | | | |
|---|---|---|---|
| 5,654,362 | 8/1997 | Schulz, Jr. et al. | 524/862 |
| 5,667,790 | 9/1997 | Sellers, Jr. | 424/401 |
| 5,674,508 | 10/1997 | Désérable et al. | 424/401 |

FOREIGN PATENT DOCUMENTS

| | | |
|---|---|---|
| 0 059 882 | 9/1982 | (EP) . |
| 0 116 406 | 8/1984 | (EP) . |
| 0 295 886 | 12/1988 | (EP) . |
| 0 692 238 | 1/1996 | (EP) . |
| 0 850 644 | 7/1998 | (EP) . |
| WO 98/00104 | 1/1998 | (WO) . |

OTHER PUBLICATIONS

Akira Matsueda et al., "Preventing Makeup Darkening During Usage", Cosmetics & Toiletries® magazine, vol. 111, Nov. 1996, pp. 35–40.

STN, Serveur de Bases de Données, Karsruhe, DE, Fichier Chemical Abstracts, vol. 105, AN–232220, XP002105483, Feb. 1996.

English language Derwent Abstract of EP 0 850 644, Dec. 24, 1996.

*Primary Examiner*—Shelley A. Dodson
(74) *Attorney, Agent, or Firm*—Finnegan, Henderson, Farabow, Garrett & Dunner, L.L.P.

(57) ABSTRACT

A composition, in particular a cosmetic composition, which can especially be in the form of an emulsion, a gel or a vesicle dispersion, the said composition comprising a pulverulent phase in an amount of less than or equal to 80% by weight relative to the total weight of the composition, this composition comprising at least one pigment and at least one antiperspirant. Use of such a composition in cosmetics, in particular for make-up, in order to improve the staying power of the color of the composition.

34 Claims, No Drawings

COSMETIC COMPOSITION COMPRISING PIGMENTS AND AN ANTIPERSPIRANT AND USE OF SUCH A COMPOSITION

The present invention relates to a cosmetic composition comprising an antiperspirant which can be used for making up the skin, semi-mucous membranes, mucous membranes and/or superficial body growths. The antiperspirant composition can be in the form of an emulsion, a gel or a vesicle dispersion.

Cosmetic compositions, in particular make-up compositions such as lipsticks, concealers or foundations, generally comprise fatty substances such as oils and waxes, and a particulate phase generally composed of fillers and pigments. They can thus be, for example in the case of lipsticks, in the form of a stick or tube or in the form of a soft paste. They are then often in the form of an anhydrous composition. Make-up compositions can also comprise water or a hydrophilic phase, and can then in particular be in the form of an oil-in-water or water-in-oil emulsion, a multiple emulsion or an aqueous solution or gel, in particular when it is a foundation, a tinted cream, a care cream or an antisun product.

The primary function of these compositions, which are first and foremost make-up products, is to beautify the human form by emphasizing, for example, the aesthetic qualities and/or by dissimulating facial imperfections.

Depending on the make-up effect which it is desired to obtain, light, discrete or, on the contrary, accentuated, the face is sometimes given a shade close to an individual's natural carnation color, and sometimes a stronger color which heightens the natural complexion: foundations are used for this. Certain reliefs can also be accentuated by providing stronger tones, for example using blushers. Sharper tones which cover all color shades are used to heighten the look. Lastly, the lips are made to stand out by giving them generally dark colors.

In all cases, the result is obtained by virtue of the presence of pigments and/or dyes in these various compositions, each of which has a quite specific function. Thus, the nature of the pigments, their color and, especially, their proportion in each of these compositions are important for obtaining the desired shade and thus the desired effect.

It is thus also important for the distribution of these pigments and/or dyes to remain constant and uniform over time, i.e. several hours after application. In order to maintain an aesthetic overall make-up effect on the face, it is of prime importance that the colors imparted by each of the compositions (foundation, blusher, eyeshadow, lipstick, etc.) at the time of their application do not become mixed.

However, it is quite often the case that the overall make-up effect deteriorates shortly after the products are applied: specifically, it has been found that certain compositions have a tendency to travel inside the wrinkles and/or fine lines in the skin, in the case of foundations; in the fine lines around the lips, in the case of lipsticks; in the folds of the eyelids, in the case of eyeshadows. The appearance of lines in the make-up, generated by the movements of the eyelids, has also been found, especially in the case of eyeshadows. The appearance of lustrous or shiny parts or alternatively the dilution of the covering power and the color can also be observed. This can be due to a multitude of factors such as, for example, heat or humidity. In particular, the distribution of the colors is no longer as uniform. Shiny parts and darkened parts can thus appear on the made-up face, and are contrary to the desired aesthetic effect.

Women nowadays desire make-up products which give them a fresh complexion and a healthy appearance throughout the day while at the same time being practical to use. Thus, they do not wish to reapply their products several times a day in order to have a permanently sharp make-up effect.

It would also be advantageous to have available a single product which could be used in summer and winter, and in hot and cold countries. Such a universal product would be very practical for women who travel, since it would save time and be less expensive.

A need thus exists for a cosmetic composition, in particular a make-up composition, which not only has good cosmetic properties but also gives the skin a coloration whose distribution remains uniform and constant over time and after application to the skin, in particular to the face.

The inventors have now discovered, surprisingly, that by introducing an antiperspirant into compositions comprising pigments, it is possible to prepare make-up compositions whose color distribution can be constant over time, in particular after application to human skin.

A subject of the invention is thus a cosmetic composition, in particular a make-up composition, comprising a pulverulent phase in an amount of less than or equal to 80% by weight, relative to the total weight of the composition. This pulverulent phase includes at least one pigment and also comprises at least one antiperspirant.

In the article "Preventing Makeup Darkening During Usage", Akira Matsueda and Tsuyoshi Ogihara, Cosmetics & Toiletries, Vol. 111, November 1996, it is taught that the secretion of sebum causes darkening of make-up products. To overcome this drawback, it is proposed to introduce a porous silica comprising a white pigment into the compositions. However, the article does not propose introducing an antiperspirant into a make-up product, in particular a product for the face, in order especially to improve the staying power of the color after application over time and to reduce the sheen of the make-up effect.

The compositions according to the invention can give the face a particularly stable coloration whose distribution can remain uniform over time, even several hours after application.

Furthermore, these compositions can have excellent staying power: preferably, they do not migrate in folds such as the eyelids or fine lines and preferably, no accumulation of product in certain areas of the face is observed. They can also show very little transfer onto supports such as glasses or clothing. They can give the skin a uniform make-up effect and a good matt effect. They can avoid making the face look sticky and can keep the face rather dry, which is particularly desired in hot and humid climates.

A subject of the invention is also the use of an antiperspirant in a cosmetic composition, in particular a make-up composition comprising at least one pigment, in order to limit, reduce or prevent the transfer and/or migration of the composition.

A subject of the invention is also the use of an antiperspirant in a cosmetic composition, in particular a make-up composition comprising at least one pigment, in order to limit, reduce or prevent the composition from transferring and/or migrating on the skin.

A subject of the invention is also the use of an antiperspirant in a cosmetic composition, in particular a make-up composition to be applied to the skin and/or mucous membranes and/or the scalp, this composition comprising at least one pigment, in order to reduce the amount of water present on the skin and/or mucous membranes and/or the scalp.

The compositions according to the invention find a particularly advantageous application especially in making up the skin, mucous membranes, semi-mucous membranes and superficial body growths. The expression "mucous membranes" especially means the inner part of the lower eyelid; the expression "semi-mucous membranes" more particularly means the lips of the face; the expression "superficial body growths" means the eyelashes, eyebrows, hair and nails. Thus, the invention can be used for make-up products for the face and the skin, such as foundations, self-tanning products or antisun products.

Another subject of the invention is a non-therapeutic process for treating the skin and/or mucous membranes and/or the scalp, in particular a make-up process, which consists in applying a composition as defined above to the skin and/or mucous membranes and/or the scalp.

Admittedly, it is known practice to use antiperspirants in compositions such as deodorants. However, nobody has hitherto used these agents for make-up compositions on the face probably because of potential problems of discomfort (irritation, tautness, etc.).

The compositions according to the invention comprise a pulverulent phase which comprises at least one pigment. The term "pigment" should be understood as meaning white or colored, inorganic or organic particles which are insoluble in the medium and are intended to color and/or opacify the composition.

The pigments can be present in an amount ranging from 0.1–30% by weight, relative to the total weight of the composition, and preferably in a proportion of 2–15%. They can be white or colored, inorganic and/or organic, and of usual or nanometric size. The inorganic pigments and nanopigments are preferably titanium dioxide, zirconium dioxide and cerium dioxide, as well as zinc oxide, iron oxide and chromium oxide, nanotitanias and ferric blue. The organic pigments are preferably carbon black and the lakes commonly employed to give the lips and the skin a make-up effect, which are calcium, barium, aluminium or zirconium salts of acidic dyes such as haloacid dyes, azo dyes or anthraquinone dyes.

These pigments can be treated so as to make their surface hydrophobic; this treatment can be carried out according to the methods known to those skilled in the art; in particular, the pigments can be coated with silicone compounds such as PDMSs and/or with polymers.

In addition to the pigments mentioned above, the pulverulent phase in the compositions according to the invention can comprise pearlescent agents and/or fillers usually used in cosmetic compositions. The term "fillers" should be understood as meaning colorless or white, inorganic or synthetic, lamellar or non-lamellar particles intended to give body or rigidity to the composition, and/or softness, a matt effect and uniformity to the make-up effect. The term "pearlescent agents" should be understood as meaning iridescent particles which reflect light.

The pearlescent agents can be present in the composition in an amount ranging from 0–20% by weight, preferably from 2–15% by weight. The pearlescent agents are preferably natural mother-of-pearl, mica coated with titanium oxide, with iron oxide, with natural pigment or with bismuth oxychloride, and colored titanium mica.

The fillers, which can be present in the composition in an amount ranging from 0–20% by weight, relative to the total weight of the composition, preferably 2–10%, can be inorganic or synthetic, and lamellar or non-lamellar. The fillers are preferably talc, mica, silica, kaolin, Nylon powder, polyethylene powder, Teflon, starch, boron nitride, microspheres such as Expancel (Nobel Industrie), microsponges such as Polytrap (Dow Coming) and silicone resin microbeads (Tospearls from Toshiba, for example).

The pulverulent phase in the compositions according to the invention is not more than 80% by weight relative to the total weight of the composition.

Preferably, the compositions according to the invention are not transparent, i.e. the characters on a sheet of newspaper cannot be seen through the composition. Preferably also, they are colored and more preferably pigmented.

The composition according to the invention also comprises an antiperspirant. The term "antiperspirant" should be understood as meaning an agent which limits the production of sweat delivered onto the skin. This antiperspirant preferably has no coloring function. This agent can be in the form of a pulverulent compound, a solution or a dispersion.

Antiperspirants according to the invention are preferably:

aluminium salts, such as aluminium chlorohydrate ($[Al_2(OH)_5Cl]nH_2O$), aluminium sesquichlorohydrate ($[Al_2(OH)_{4.5}Cl_{1.5}]nH_2O$), aluminium dichlorohydrate ($[Al_2(OH)_4Cl_2]nH_2O$, aluminium chlorohydrex propylene glycol (PG) or polyethylene glycol (PEG) ($[Al_2(OH)_5Cl]nH_2O+CH_3CHOHCH_2OH$ or $H(OCH_2(CH_2)nOH)$), aluminium sesquichlorohydrex PG or PEG, aluminium PG or PEG dichlorohydrex and aluminium hydroxide ($Al(OH)_3nH_2O$), aluminium zirconium chlorohydrates, such as aluminium zirconium trichlorohydrate ($[Al_{3.8}Zr(OH)_{12.4}Cl_3]nH_2O$), aluminium zirconium tetrachlorohydrate ($[Al_{3.6}Zr(OH)_{11.6}Cl_{3.2}]nH_2O$), aluminium zirconium pentachlorohydrate ($[Al_8Zr(OH)_{23}Cl_5]nH_2O$), aluminium zirconium octachlorohydrate ($[Al_8Zr(OH)_{20}Cl_8]nH_2O$, aluminium zirconium trichlorohydrex glycine ($[Al_{3.8}Zr(OH)_{12.4}Cl_3]nH_2O+H_2NCH_2COOH$), aluminium zirconium tetrachlorohydrex glycine, aluminium zirconium pentachlorohydrex glycine and aluminium zirconium octachlorohydrex glycine, potassium aluminium sulphate, also known as alum ($KAl(SO_4)_2 12H_2O$), aluminium undecylenoyl collagen amino acid, sodium aluminium lactate+aluminium sulphate ($Al_2(SO_4)_3+Na_2HAl(OOCCHOHCH_3)_2—(OH)_6$), sodium aluminium chlorohydroxylactate, aluminium bromohydrate ($Al_2Br(OH)_5nH_2O$), aluminium chloride ($AlCl_3 6H_2O$), complexes of zinc salt and of sodium salt, complexes of lanthanum and cerium, and the aluminium salt of lipoamino acids ($R—CO—NH—CHR'—CO—OAl—(OH)_2$ with $R=C_6/C_{11}$ and $R'$=amino acid).

Preferably, the antiperspirant is an aluminium salt and, more preferably, it is chosen from potassium aluminium sulphate (alum) and aluminium chlorohydrate.

Preferably, the compositions of the invention comprise an effective amount of antiperspirant to limit the migration of the make-up on the skin after this make-up has been applied.

Thus, the antiperspirant is generally present in the compositions of the invention in an amount ranging from 0.1 to 30% by weight, relative to the total weight of the composition, preferably from 1 to 10% by weight relative to the total weight of the composition.

The compositions of the invention also contain a cosmetically, hygienically, pharmaceutically or dermatologically acceptable medium, i.e. a medium which is compatible with all keratin substances such as the skin, the nails, the hair, the eyelashes and the eyebrows, mucous membranes and semi-mucous membranes, and any other area of body or facial skin.

The compositions of the invention can thus be in the form of an oil-in-water (O/W) emulsion, a water-in-oil (W/O) emulsion, a multiple emulsion or a multi-phase solution. They can also be in the form of an aqueous gel or an aqueous, aqueous-alcoholic or multiphase solution. They can also be in the form of an anhydrous gel.

The compositions of the invention can also be in the form of a vesicle dispersion, for example in the form of an oily phase dispersed in an aqueous phase and stabilized with liposomes.

When the composition is in the form of an aqueous solution or gel, it can also comprise water-soluble dyes chosen from the dyes which are common in the sector considered, such as the disodium salt of ponceau, the disodium salt of alizarin green, quinoline yellow, the trisodium salt of amaranth, the disodium salt of tartrazine, the monosodium salt of rhodamine, the disodium salt of fuchsin, and xanthophyll.

When the composition is in the form of an O/W emulsion, the antiperspirant content can range, for example, from 1 to 5%; when the composition is in the form of a W/O emulsion, this content can range from 1 to 10%; when the composition is in the form of an aqueous gel, this content can range from 1 to 5%; when the composition is in the form of an anhydrous gel, this content can range from 1 to 30%, all weight percentages being relative to the total weight of the emulsion.

This content is preferably chosen by a person skilled in the art in order to obtain stable compositions, irrespective of the form of these compositions.

When the composition according to the invention comprises an aqueous phase, the latter phase can comprise water, a floral water such as cornflower water and/or a mineral water such as eau de Vittel, eau de Lucas or eau de La Roche Posay and/or a spring water.

When the composition according to the invention comprises a fatty phase, the latter phase can consist in particular of fatty substances which are liquid at 25° C., such as oils of animal, plant, mineral or synthetic origin.

When the composition according to the invention is in the form of an emulsion, the fatty phase can comprise any cosmetically acceptable oil, provided that, when mixed with the aqueous phase and the optional additives, the oil gives a stable emulsion, i.e. an emulsion which does not break and which remains in the form of a single phase for at least 24 hours after storage at 25° C., without any phenomenon of creaming or release of oil.

The oils which can be used can optionally be volatile at room temperature (20–25° C.). The expression "volatile oil" means any compound which can evaporate on contact with the skin. Preferably, oils are used whose flashpoint is high enough to allow them to be used in formulation.

These volatile compounds can be chosen in particular from cyclic or linear, hydrocarbon-based and/or silicone oils, alone or as a mixture. For example, the volatile silicone oils can be:

cyclic volatile silicones containing from 3 to 8 and preferably from 4 to 6 silicon atoms. Examples of these are cyclotetradimethylsiloxane, cyclopentadimethylsiloxane and cyclohexadimethylsiloxane, cyclocopolymers of the dimethylsiloxane/methylalkylsiloxane type, such as Silicone FZ 3109 sold by the company Union Carbide, which is a dimethylsiloxane/methyloctylsiloxane cyclocopolymer, linear volatile silicones containing from 2 to 9 silicon atoms. Examples of these are hexamethyldisiloxane or a PDMS of low viscosity (1 cSt). Mention may also be made of alkyltrisiloxanes such as hexylheptamethyltrisiloxane or octylheptamethyltrisiloxane.

Hydrocarbon-based volatile oils include isoparaffins and in particular isododecane.

The non-volatile oils may be:

poly($C_1$–$C_{20}$)alkylsiloxanes and in particular those containing trimethylsilyl end groups, preferably those whose viscosity is less than 0.06 $m^2$/s, among which mention may be made of linear polydimethylsiloxanes and alkylmethylpolysiloxanes such as cetyldimethicone (CTFA name), silicones modified with aliphatic and/or aromatic groups, which may contain fluorine, or with functional groups such as hydroxyl, thiol and/or amine groups, phenylsilicone oils, oils of animal, plant or mineral origin, such as liquid paraffin, liquid petroleum jelly, perhydrosqualene, apricot oil, wheatgerm oil, sweet almond oil, beauty-leaf oil, sesame oil, macadamia oil, grapeseed oil, rapeseed oil, coconut oil, groundnut oil, palm oil, castor oil, avocado oil, jojoba oil, olive oil or cereal germ oil; fatty acid esters of polyols, in particular liquid triglycerides; alcohols; acetylglycerides; alkyl or polyalkyl octanoates, decanoates or ricinoleates; fatty acid triglycerides; glycerides, fluoro oils and perfluoro oils;

mixtures thereof.

The composition according to the invention can also comprise other fatty substances, which can be chosen by a person skilled in the art on the basis of his or her general knowledge, so as to give the final composition the desired properties, for example in terms of consistency, texture and/or transfer. These additional fatty substances can be waxes, gums and/or pasty fatty substances of animal, plant, mineral or synthetic origin, as well as mixtures thereof.

For example, these additional fatty substances can be:

silicone gums, waxes of animal, plant, mineral or synthetic origin, such as microcrystalline waxes, paraffin, petrolatum, petroleum jelly, ozocerite, montan wax; beeswax, lanolin and its derivatives; candelilla wax, Ouricury wax, carnauba wax, Japan wax, cocobutter, cork fibre wax or sugarcane wax; hydrogenated oils which are solid at 25° C., ozocerites, fatty esters and glycerides which are solid at 25° C.; polyethylene waxes and waxes obtained by Fischer-Tropsch synthesis; hydrogenated oils which are solid at 25° C.; lanolins; fatty esters which are solid at 25° C.; silicone waxes; fluoro waxes; mixtures thereof.

When the composition according to the invention is in the form of an emulsion, it can also optionally comprise a surfactant. The O/W surfactants are preferably (CTFA): cetearylglucoside, PEG40 stearate, sorbitan tristearate, sorbitan stearate, polysorbate 60, sorbitan stearate/sucrose cocoate mixture, the glyceryl stearate/PEG-100 stearate mixture, PEG400, glyceryl stearate, the PEG-6/PEG-32/glycol stearate mixture, triethanolamine stearate, sodium stearate. W/O surfactants which may be mentioned in particular are the polyglyceryl-4 isostearate/cetyldimethicone copolyol/hexyl laurate mixture, the mineral oil/petrolatum/ozocerite/glyceryl oleate/lanolin alcohol mixture, dimethicone copolyols, cetyldimethicone copolyols, $\alpha,\omega$-substituted copolyols, i.e. copolyols substituted at the two ends of the silicone chain. $\alpha,\omega$-substituted dimethicone copolyols are preferably used.

In a preferred embodiment, the composition according to the invention is in the form of a W/O emulsion.

The composition according to the invention can also comprise 0 to 5% by weight, relative to the total weight of the emulsion, of at least one co-emulsifier which can be chosen from oxyethylenated sorbitan monostearate, fatty alcohols such as stearyl alcohol and cetyl alcohol, and fatty acid esters of polyols, such as glyceryl stearate and polyglyceryl 10-decaoleate.

In addition, the composition according to the invention can comprise one or more thickeners.

The composition can also comprise any additional compound usually used in cosmetics, such as antioxidants, fragrances, essential oils, preserving agents, lipophilic or hydrophilic cosmetic or pharmaceutical active agents, moisturizers, vitamins, essential fatty acids, sphingolipids, self-tanning compounds such as DHA, and sunscreens.

Needless to say, a person skilled in the art will take care to select this or these optional additional compound(s), and/or the amount thereof, such that the advantageous properties of the composition according to the invention are not, or are not substantially, adversely affected by the addition envisaged.

These additional compounds can be present in the composition in a proportion of 0–10% by weight. Depending on their nature, they can be present in the aqueous phase or in the fatty phase of the composition.

The compositions according to the invention can be in any form which is suitable for topical application, in particular in the form of a stick, lotion, cream, milk or gel which is aqueous or anhydrous, emulsions obtained by dispersing a fatty phase in an aqueous phase (O/W) or, conversely, (W/O), of liquid or semi-liquid consistency, or even pasty or solid consistency.

The compositions according to the invention can be in the form of a cosmetic make-up product, in particular a product for making up the skin and/or mucous membranes and/or the scalp, in particular for the body and/or the face, such as, for example, a foundation, a face powder, an eyeshadow, an eyeliner, a mascara or a lipstick.

The compositions according to the invention can form all or part of a cosmetic, pharmaceutical or hygiene composition.

The compositions according to the invention can be prepared according to the standard methods for preparing W/O or O/W emulsions or aqueous or anhydrous gels, these methods being well known to those skilled in the art.

The invention is illustrated in greater detail in the examples which follow. In all these examples, the amounts are expressed as a percentage by weight relative to the total weight of the composition.

EXAMPLE 1

The inventors prepared the W/O emulsion below:

Foundation:

| | |
|---|---|
| polyglyceryl-4 isostearate/cetyldimethicone copolyol/hexyl laurate mixture sold under the trade name "Abil WE 09" by Goldschmidt | 5% |
| cyclopentasiloxane | 20% |
| apricot oil | 5% |
| PDMS-coated pigments | 8% |
| preserving agent | qs |
| aluminum hydroxide (antiperspirant) | 10% |
| water | qs 100% |

This composition was prepared in the following way: each of the aqueous and oily phases was prepared separately by mixing together the various components. The aqueous phase was then incorporated into the oily phase without heating and with stirring. At least the pigments and antiperspirant are contained in the pulverulent phase.

This composition is stable over time. After application to the face, the distribution of the color remains constant, even in a hot and humid climate and after several hours under these conditions.

EXAMPLE 2

The inventors prepared the W/O emulsion below:

| | |
|---|---|
| α,ω-substituted oxyethylenated, oxypropylenated silicone/cyclomethicone mixture (85/15) sold under the trade name "Abil EM 97" by Goldschmidt | 6.3% |
| isostearyl diglyceryl succinate sold under the trade name "Inwitor by 780 K" Hüls | 2% |
| cyclopentasiloxane | 19.35% |
| pigments | 7% |
| volatile cyclopentasiloxane oil | 3.5% |
| alum (antiperspirant) | 2% |

This composition was prepared according to the same preparation process as for the composition of Example 1.

This composition is stable over time. After application to the face, the distribution of the colour remains constant, even in a hot and humid climate and after several hours under these conditions.

EXAMPLE 3

The inventors prepared the O/W emulsion below:

| | |
|---|---|
| stearic acid | 4.9% |
| triethanolamine | 1% |
| plant oils | 14.15% |
| cyclopentasiloxane | 5% |
| polydimethylsiloxane 10 cst | 4% |
| talc | 8% |
| magnesium aluminum silicate sold under the trade name "Veegum" by Vanderbilt | 2.56% |
| carboxymethylcellulose | 0.14% |
| pigments | 16% |
| hydrating agent | 6% |
| aluminum chlorohydrate (antiperspirant) | 2% |
| preserving agent | qs |
| water | qs 100% |

The composition was prepared according to the standard methods for preparing O/W emulsions, which are well known to those skilled in the art. At least the pigments and antiperspirant are contained in the pulverulent phase.

EXAMPLE 4

Comparative

The inventors prepared 2 water-in-oil emulsions A (comparative) and B (invention) such that:

Composition:

| | |
|---|---|
| α,ω-substituted oxyethylenated, oxypropylenated silicone/cyclomethicone mixture (85/15) sold under the trade name "Abil EM 97" by Goldschmidt | 6.3% |
| isostearyl diglyceryl succinate sold under the trade name "Inwitor 780 K" by Hüls | 2% |

-continued

| | |
|---|---|
| polydimethylsiloxane sold under the trade name "Mirasil C. DPDM" by Rhodia Chemie | 8% |
| PDMS-coated pigments | 7% |
| cyclopentasiloxane | 3.5% |
| smectite | 4% |
| Nylon powder | 8% |
| $MgSO_4$ | 0.7% |
| preserving agent | qs |
| antiperspirant | x % |
| water | qs 100% |

| Composition | Antiperspirant | x % |
|---|---|---|
| Composition A (Comparative) | NO | 0 |
| Composition B (Invention) | Potassium aluminum sulphate $12H_2O$ | 5 |

In composition A, at least the pigments are contained in the pulverulent phase. In composition B, at least the pigments and antiperspirant are contained in the pulverulent phase.

The inventors performed moisturization tests on a panel of seven models, who perspire under warm conditions, placed in a room at a temperature of about 30° C. and 50% relative humidity. The moisturization on the skin was measured in triplicate, on each model, using an SEI-M-0034-COMB-02 corneometer, wiping the corneometer probe between each measurement. These measurements were taken at T0 (at the time of application of the product), after 15 minutes (T15), after 1 h 30 min (T1h30) and after 3 h (T3h). The averages of the values read on the corneometer are given in the table below:

| | T0 | T15 | T1h30 | T3h |
|---|---|---|---|---|
| Composition A | 111.86 ± 18.90 | 96.30 ± 15.60 | 108.90 ± 18.10 | 114.09 ± 16.55 |
| Composition B | 119.38 ± 15.49 | 91.50 ± 16.30 | 102.14 ± 11.94 | 110.95 ± 14.28 |

It is seen that, from 15 minutes and up to 3 hours, the hydration measured with the corneometer is lower for composition B according to the invention than for composition A not in accordance with the invention, this being despite the fact that, at T0, the hydration measured for composition B was higher. Composition B according to the invention thus reduces the amount of water present at the surface of the skin, thereby contributing towards preventing the sticky sensation which can usually be experienced in a hot and humid atmosphere.

Composition B migrates very little on the face, and no accumulation of the product is found in the folds of the skin, even after several hours.

Furthermore, composition B gives a more matte complexion than composition A, which gives a shiny complexion.

EXAMPLE 5

Comparative

The inventors prepared composition C according to the invention, corresponding to composition B of Example 4 in which the 5% of potassium aluminium sulphate dodecahydrate were replaced with 20% of aluminium chlorohydrate.

The inventors then evaluated the transfer of compositions A and C according to the following procedure: 2 hours 30 minutes after applying the compositions, a ring of fabric was placed on the faces of six individuals for 30 minutes. The deposition of foundation on the rings was then visualized. The results are collated in the table below:

| Result | Composition A (Comparative) | Composition C (Invention) |
|---|---|---|
| None | — | — |
| Traces | — | 1 |
| Traces+ | — | — |
| Light | 2 | 4 |
| Light+ | 3 | — |
| Moderate | 1 | 1 |
| Moderate+ | — | — |
| Heavy | — | — |
| Total for the tests | 6 | 6 |
| Score (average grade) | 3.8 | 3 |

It is seen from this table that composition C according to the invention transfers less than composition A which comprises no antiperspirant.

Furthermore, composition C gives the skin a more matte, less shiny complexion than composition A. The film formed on the skin by composition C is also more uniform: in contrast, with composition A, the formation of plaques is observed, giving an unappealing marbled appearance.

What is claimed is:

1. A cosmetic composition, comprising:
    a pulverulent phase in an amount less than or equal to 80% by weight, relative to the total weight of the composition;
    at least one pigment; and
    at least one antiperspirant.

2. The composition according to claim 1, wherein said at least one pigment is present in said composition in an amount ranging from 0.1 to 30% by weight, relative to the total weight of the composition.

3. The composition according to claim 2, wherein the pigment amount ranges from 2 to 15%.

4. The composition according to claim 1, wherein the at least one pigment is chosen from titanium dioxide, zirconium dioxide, cerium dioxide, zinc oxide, iron oxide, chromium oxide, nanotitanias, ferric blue, carbon black and calcium, barium, aluminium and zirconium salts of acidic dyes.

5. The composition according to claim 4 wherein said salts of acidic dyes are chosen from salts of haloacid dyes, azo dyes and anthraquinone dyes.

6. The composition according to claim 1, wherein said composition is not transparent.

7. The composition according to claim 1, wherein said at least one antiperspirant is chosen from:
    aluminium salts,
    aluminium zirconium chlorohydrates,
    potassium aluminium sulphate of structure $KAl(SO_4)_2 12H_2O$, aluminium undecylenoyl collagen amino acid, sodium aluminium lactate+aluminium sulphate of structure $Al_2(SO_4)_3+Na_2HAl(OOCCHOHCH_3)_2—(OH)_6$, sodium aluminium chlorohydroxylactate, aluminium bromohydrates of structure $Al_2Br(OH)_5nH_2O$, aluminium chloride of structure $AlCl_36H_2O$, complexes of zinc salt and of sodium salt, and complexes of lanthanum and cerium.

8. The composition according to claim 1, wherein said at least one antiperspirant is chosen from aluminium chlorohydrates of structure $(Al_2(OH)_5Cl)nH_2O$, aluminium sesquichlorohydrates of structure $(Al_2(OH)_{4.5}Cl_{1.5})nH_2O$, aluminium dichlorohydrate of structure $(Al_2(OH)_4Cl_2)nH_2O$, aluminium chlorohydrex propylene glycol of structure $(Al_2(OH)_5Cl)nH_2O+CH_3CHOHCH_2OH$, aluminium chlorohydrex polyethylene glycol of structure $(Al_2(OH)_5Cl)nH_2O+H(OCH_2(CH_2)nOH)$, aluminium sesquichlorohydrex propylene glycol, aluminium sesquichlorohydrex polyethylene glycol, aluminium propylene glycol dichlorohydrex, aluminium polyethylene glycol dichlorohydrex, aluminium hydroxide of structure $Al(OH)_3nH_2O$, and the aluminium salts of lipoamino acids.

9. The composition according to claim 1, wherein said at least one antiperspirant is chosen from aluminium zirconium trichlorohydrate of structure $(Al_{3.8}Zr(OH)_{12.4}Cl_3)nH_2O$, aluminium zirconium tetrachlorohydrate of structure $(Al_{3.6}Zr(OH)_{11.6}C_{3.2})nH_2O$, aluminium zirconium pentachlorohydrate of structure $(Al_8Zr(OH)_{23}Cl_5)nH_2O$, aluminium zirconium octachlorohydrate of structure $(Al_8Zr(OH)_{20}Cl_8)nH_2O$, aluminium zirconium trichlorohydrex glycine of structure $(Al_{3.8}Zr(OH)_{12.4}Cl_3)nH_2O+H_2NCH_2COOH$, aluminium zirconium tetrachlorohydrex glycine, aluminium zirconium pentachlorohydrex glycine and aluminium zirconium octachlorohydrex glycine.

10. The composition according to claim 1 wherein said at least one antiperspirant is sodium aluminium lactate+aluminium sulphate.

11. The composition according to claim 1, wherein said at least one antiperspirant is chosen from aluminium salts.

12. The composition according to claim 11, wherein said at least one antiperspirant is chosen from potassium aluminium sulphate and aluminium chlorohydrate.

13. The composition according claim 1, wherein the at least one antiperspirant is present in the composition in an amount ranging from 0.1 to 30% by weight relative to the total weight of the composition.

14. The composition according to claim 1, wherein said composition is in the form of a W/O emulsion.

15. A composition according to claim 1, wherein said composition is a product for application to the body or face.

16. A foundation, comprising:
    at least one pigment; and
    at least one antiperspirant.

17. The foundation according to claim 16, further comprising a pulverulent phase in an amount less than or equal to 80% by weight, relative to the total weight of the composition.

18. A face powder, comprising:
    at least one pigment; and
    at least one antiperspirant.

19. The face powder according to claim 18, further comprising a pulverulent phase in an amount less than or equal to 80% by weight, relative to the total weight of the composition.

20. An eyeshadow, comprising:
    at least one pigment; and
    at least one antiperspirant.

21. The eyeshadow according to claim 20, further comprising a pulverulent phase in an amount less than or equal to 80% by weight, relative to the total weight of the composition.

22. An eyeliner, comprising:
    at least one pigment; and
    at least one antiperspirant.

23. The eyeliner according to claim 22, further comprising a pulverulent phase in an amount less than or equal to 80% by weight, relative to the total weight of the composition.

24. A mascara comprising:
    at least one pigment; and
    at least one antiperspirant.

25. The mascara according to claim 24, further comprising a pulverulent phase in an amount less than or equal to 80% by weight, relative to the total weight of the composition.

26. A lipstick, comprising:
    at least one pigment; and
    at least one antiperspirant.

27. The lipstick according to claim 26, further comprising a pulverulent phase in an amount less than or equal to 80% by weight, relative to the total weight of the composition.

28. A cosmetic make-up composition, comprising:
    at least one pigment, and
    at least one antiperspirant in an amount effective to limit, reduce or prevent the transfer from an object of application to a support, or migration on the object of application, of said composition.

29. The cosmetic composition of claim 28, wherein said composition is for application to the skin.

30. A cosmetic make-up composition for application to skin, mucous membranes or a scalp, comprising:
    at least one pigment, and
    at least one antiperspirant in an amount effective to reduce the amount of water present on the skin, mucous membranes or the scalp.

31. A non-therapeutic process for treating skin, mucous membranes, or a scalp, comprising:
    applying to the skin, mucous membranes, or scalp, a composition comprising a pulverulent phase in an amount less than or equal to 80% by weight, relative to the total weight of the composition, at least one pigment, and at least one antiperspirant.

32. The composition according to claim 1, wherein the pulverulent phase is present in an amount of at least 0.1% by weight, relative to the total weight of the composition.

33. The composition according to claim 1, said composition being in the form of an emulsion, a gel or a vesicle dispersion.

34. The composition according to claim 1, wherein said at least one antiperspirant is chosen from: potassium aluminium sulphate of structure $KAl(SO_4)_2 12H_2O$, aluminium undecylenoyl collagen amino acid, sodium aluminium lactate+aluminium sulphate of structure $Al_2(SO_4)_3+Na_2HAl(OOCCHOHCH_3)_2—(OH)_6$, sodium aluminium chlorohydroxylactate, aluminium bromohydrates of structure $Al_2Br(OH)_5nH_2O$, aluminium chloride of structure $AlCl_3 6H_2O$, complexes of zinc salt and of sodium salt, complexes of lanthanum and cerium, aluminium chlorohydrates of structure $(Al_2(OH)_5Cl)nH_2O$, aluminium sesquichlorohydrates of structure $(Al_2(OH)_{4.5}Cl_{1.5})nH_2O$, aluminium dichlorohydrate of structure $(Al_2(OH)_4Cl_2)nH_2O$, aluminium chlorohydrex propylene glycol of structure $(Al_2(OH)_5Cl)nH_2O+CH_3CHOHCH_2OH$, aluminium chlorohydrex polyethylene glycol of structure $(Al_2(OH)_5Cl)nH_2O+H(OCH_2(CH_2)nOH)$, aluminium sesquichlorohydrex propylene glycol, aluminium sesquichlorohydrex polyethylene glycol, aluminium propylene glycol dichlorohydrex, aluminium polyethylene glycol dichlorohydrex, aluminium hydroxide of structure $Al(OH)_3nH_2O$, aluminium salts of lipoamino acids, aluminium zirconium trichlorohydrate of structure $(Al_{3.8}Zr(OH)_{12.4}Cl_3)nH_2O$, aluminium zirconium tetrachlorohydrate of structure $(Al_{3.6}Zr(OH)_{11.6}Cl_{3.2})nH_2O$, aluminium zirconium pentachlorohydrate of structure $(Al_8Zr(OH)_{23}Cl_5)nH_2O$, aluminium zirconium octachlorohydrate of structure $(Al_8Zr(OH)_{20}Cl_8)nH_2O$, aluminium zirconium trichlorohydrex glycine of structure $(Al_{3.8}Zr(OH)_{12.4}Cl_3)nH_2O+H_2NCH_2COOH$, aluminium zirconium tetrachlorohydrex glycine, aluminium zirconium pentachlorohydrex glycine and aluminium zirconium octachlorohydrex glycine.

* * * * *